(12) United States Patent
Zhang

(10) Patent No.: US 9,089,595 B2
(45) Date of Patent: Jul. 28, 2015

(54) **EXTRACT OF *REHMANNIA GLUTINASA LIBOSCH.* FOR REDUCING BLOOD GLUCOSE AND LIPID LEVELS AND TREATING HEMATOLOGIC DISEASES, AND METHODS FOR PREPARING THE SAME**

(76) Inventor: Ling Zhang, Beijing (CN)

( * ) Notice: Subject to any disclaimer, the term of this patent is extended or adjusted under 35 U.S.C. 154(b) by 91 days.

(21) Appl. No.: 12/669,340

(22) PCT Filed: Jun. 27, 2008

(86) PCT No.: PCT/CN2008/001242
§ 371 (c)(1),
(2), (4) Date: Jan. 29, 2010

(87) PCT Pub. No.: WO2009/009952
PCT Pub. Date: Jan. 22, 2009

(65) Prior Publication Data
US 2010/0197618 A1    Aug. 5, 2010

(30) Foreign Application Priority Data
Jul. 18, 2007   (CN) .......................... 2007 1 0130252

(51) Int. Cl.
*A61K 31/7004*    (2006.01)
*A61K 36/804*    (2006.01)

(52) U.S. Cl.
CPC .................... *A61K 36/804* (2013.01)

(58) Field of Classification Search
None
See application file for complete search history.

(56) References Cited

U.S. PATENT DOCUMENTS

2005/0019435 A1*  1/2005 Young .......................... 424/756

FOREIGN PATENT DOCUMENTS

| CN | 1317337 A | 10/2001 |
|---|---|---|
| CN | 1715285 A | 1/2006 |
| CN | 200410062245 | 1/2006 |
| CN | 101003551 A | 7/2007 |
| CN | 101099789 A | 1/2008 |
| CN | 101220063 A | 7/2008 |

OTHER PUBLICATIONS

Guo et al. J Chin Integr Med, Mar. 2004, vol. 2, No. 2, pp. 135-137.*
Qingfeng et al. J of Radioimmunology 2004, 17(5), pp. 358-360.*
Zhang et al. Pharmacology, Biochemistry and Behavior 88 (2007) 64-72, published online Jul. 18, 2007.*
Wang, Huisen et al.; "Separation and identification of Iridoid Glycoside in fresh *Rehmannia glotinasa* Libosa"; *Traditional Chinese Medicinal Research*; Apr. 2005: vol. 18, No. 4, 17-19.
Wang, Chengyuan et al.; "Technologies for Purification and Separation of Iridoid Glycosides from Dried *Rehmannia* Root"; *Herald of Medicine*; Oct. 2003; vol. 22, No. 10, 707-709.
Zhang, Tingguang at al.; "Technology of separation and purification of catalpol in *Rehmannia glutinasa* Libosch"; *Chinese Journal of Chinese Materia Medica*; Jun. 2004; vol. 29, No. 6.
Wang, Chengyuan et al; "Separation and Purification of glycosides and saccharides by macroporous adsorption resin"; *Journal of Chinese Medicinal Materials*; Mar. 2003; vol. 26, No. 3, 202-204.
Liu, Ming et al.; "Technological Process for Catapol of *Rehmannia glutinosa* Libosch"; *Lishizhen Medicine and Materia Medica Research*; 2000; vol. 11, No. 4, 301-302.
International Search Report ofInternational Application PCT/CN2008/001242 dated Sep. 25, 2008.
International Search Report for International application No. PCT/CN2008/001242; Date of mailing: Sep. 25, 2008.

* cited by examiner

*Primary Examiner* — Layla Bland
(74) *Attorney, Agent, or Firm* — Frommer Lawrence & Haug LLP; William S. Frommer; Kathleen N. Ehrhard

(57) ABSTRACT

The present invention relates to a *Rehmannia glutinasa Libosch.* extract for reducing blood glucose and lipid levels and treating hematologic diseases such as leukemia, and methods for preparing the same. The extract is prepared by subjecting fresh *Rehmannia glutinasa Libosch.* to flux extraction, concentrating the resultant extract, dissolving the concentrated extract with water, loading the obtained solution on a column packed with macroporous adsorption resins, eluting the column with ethanol, concentrating and drying the eluate. The extract can be made into clinically acceptable forms of dosage by pharmaceutically conventional measures, including capsule, tablet, pill, granule, dropping pill and so on. The extract is stable and has catalpol content up to 90-98%. The preparing method is simple to operate and applicable to industrial-scale production.

17 Claims, No Drawings

EXTRACT OF *REHMANNIA GLUTINASA LIBOSCH.* FOR REDUCING BLOOD GLUCOSE AND LIPID LEVELS AND TREATING HEMATOLOGIC DISEASES, AND METHODS FOR PREPARING THE SAME

TECHNICAL FIELD

The present invention relates to an extract from Chinese materia medica (CMM) and methods for preparing the same. More particularly, the present invention relates to an effective fraction of *Rehmannia glutinasa Libosch.* for treating hyperglycemia, hyperlipidemia and hematologic diseases like leukaemia, its preparation and methods for preparing the same.

BACKGROUND ART

With the development of social economy, great changes have taken place in people's life style and dietary choices, which thus results in dramatic changes in spectrum of diseases, and chronic non-infectious diseases are becoming prominent problems endangering people's physical and spiritual health. Among these diseases, hyperglycemia, hyperlipidemia and leukaemia are on the rise, and epidemiological studies have shown that hyperlipidemia, hypertension and diabetes are closely associated with atherosclerosis. More seriously, hyperlipidemia, hypertension and hyperglycemia often come together, which has gradually become one of the important health hazards worldwide.

As one type of commonly used CMM, raw *Rehmannia glutinasa Libosch.* is the fresh tuber of *Rehmannia glutinasa Libosch* of Scrophulariaceae family with wide clinical applications, such as treating hematologic diseases by enriching, cooling and regulating blood. As known in China, *Rehmannia glutinasa Libosch.* is usually used for treating such diseases as heat diseases and deep-red tongue, interior heat and diabetes, efficiency of liver-yin and kidney-yin, hectic fever and so on. In recent years, many researches have been carried out on the chemical composition and pharmacological action of *Rehmannia glutinasa Libosch.* It is reported that *Rehmannia glutinasa Libosch.* has various biological activities on the systems of immune, endocrine and blood, the cardio-cerebral vascular system, the nervous system and so on. As the main components, phytosterols, carbohydrates, amino acids, iridoid glycosides such as catalpol and the like are included in *Rehmannia glutinasa Libosch.*

After extensive studies and experiments, the present applicant found that as one type of main components in *Rehmannia glutinasa Libosch.*, iridoid glycosides such as catalpol and the like are highly polar compounds with similar chemical structures, which have low chemical and thermal stability and are difficult to be extracted and separated. As a result, there is no *Rehmannia glutinasa Libosch.* extract in the existing products that has a definite main effective composition, contains high content of catalpol, and has high stability and reliable efficacy in reducing blood glucose and blood lipid.

DISCLOSURE OF INVENTION

In medicine field, "effective fraction" of CMM refers to non-single chemical components extracted from Chinese medicinal materials, natural materia medica and compounded Chinese materia medica, including total flavonoids, total alkaloids, etc. One or more kinds of such chemical component should have a content of over 50% based on the total extracts and one or more kinds of such known chemical component should be regarded as effective components. And it is necessary for an effective fraction as a whole to have clear chemical constitution (one kind or several kinds of substances) with its composition and content definite and stable, and to have one to two kinds of definite main effective component.

An object of the present invention is to provide an effective fraction of *Rehmannia glutinasa Libosch.* that has reliable efficacy in reducing blood glucose, lipid levels and treating hematologic diseases such as leukaemia, and of which the effective component is specific and has high content and stability.

Another object of the present invention is to provide a method for preparing the effective fraction of *Rehmannia glutinasa Libosch.*, which is advantageous over the prior art in respect of being reliable, repeatable, and simple for operation, and is suitable for producing on an industrial scale.

A further object of the present invention is to provide medicaments of various dosage forms made from the effective fraction of *Rehmannia glutinasa Libosch.*

Specifically, the present invention is implemented by the following technical solutions:

The present invention provides an effective fraction of *Rehmannia glutinasa Libosch.* that has reliable efficacy in reducing blood glucose and lipid levels and treating hematologic diseases such as leukaemia, characterized in that the content of catalpol in the effective fraction is not lower than 50%, preferably 90-99.8%. The effective fraction of *Rehmannia glutinasa Libosch.* according to the present invention is white and non-odor crystal.

More preferably, the content of catalpol in the effective fraction of *Rehmannia glutinasa Libosch.* according to the present invention is 96%.

The effective fraction of *Rehmannia glutinasa Libosch.* according to the present invention is prepared by the following method:

Overground or underground parts of fresh *Rehmannia glutinasa Libosch.* were extracted with water or ethanol, and the resultant extract liquid was concentrated to obtain extract; after the extract was dissolved with water, the result solution was subjected to filtration; the filtrate was loaded on a column packed with macroporous adsorption resin, followed by eluted with water until water eluate became clear, and then gradiently eluted with ethanol; finally the eluate was recovered, concentrated and dried, thus the effective fraction of *Rehmannia glutinasa Libosch.* according to the present invention is obtained. The content of catalpol in such effective fraction should be not lower than 50%, and the optimum content was up to 90-99.8%.

In the present invention, the raw material used for extraction is the overground stem and leaves or underground tuber of fresh *Rehmannia glutinasa Libosch.* Extraction solvent is water or ethanol. The macroporous adsorption resins are selected from non polar or weak polar resins, such as H103, D101, HP10, HP-20, HP-21, AB-8, D101 type, D201 type, AB-8 type, HPD-100, HPD-200, HPD-100A and the like. The elution is gradiently eluted with water and ethanol (10-90%); and the eluate is concentrated and dried under vacuum, with the temperature controlled at 50-750° C.

A detailed method for preparing the effective fraction of *Rehmannia glutinasa Libosch.* according to the present invention is shown below:

Sliced fresh *Rehmannia glutinasa Libosch.* is extracted at 60-80° C. with 20-50% ethanol for 2-5 hours; then the ethanol is recovered and the extract liquid is concentrated to such an extent that there is no odor of ethanol to obtain extract; after the extract is dissolved with water of 4-6 times the weight of the raw material, the resultant solution is filtered, and then the filtrate is loaded on a column packed with macroporous adsorption resin of 1-3 times the weight of the raw material; the column is firstly eluted with water until water eluate becomes clear, followed by eluted with 10-40% ethanol of 30-50 times the weight of the raw material, then the finally the ethanol eluate is recovered, concentrated and dried, thus the effective fraction of *Rehmannia glutinasa Libosch.* is obtained. The content of catalpol in this effective fraction is 90-99.8%.

The most preferable method for preparing the effective fraction of *Rehmannia glutinasa Libosch.* according to the present invention is as follows:

The fresh *Rehmannia glutinasa Libosch.* is sliced into sheets about 1 cm in thickness, and the sheets are extracted at 75° C. with 30% ethanol for 3 hr; then the ethanol is recovered and the extract liquid is concentrated to such an extent that there is no odor of ethanol to obtain extract; after the extract is dissolved with water of 5 times the weight of the raw material, the resultant solution is filtrated, and then the filtrate is loaded on a column packed with H103 macroporous adsorption resin of twice the weight of the raw material; the column is firstly eluted with water until water eluate becomes clear, followed by eluted with 20% ethanol of 40 times the weight of the raw material. Finally the ethanol eluate is recovered, concentrated, and dried at 60° C., thus the effective fraction of *Rehmannia glutinasa Libosch.* is obtained. The content of catalpol in this effective fraction is 96%.

The above-mentioned effective fraction of *Rehmannia glutinasa Libosch.* can be further made into clinically acceptable dosage forms by pharmaceutically conventional method, such as capsule, tablet, granule, pill, oral liquid preparation, dropping pill, suppository, injection and so on.

Study on Extraction Process

I. The Selection of Raw Material

*Rehmannia glutinasa Libosch.* is the tuber of *Rehmannia glutinasa Libosch* of Scrophulariaceae family, usually classified into two categories, i.e. raw *Rehmannia glutinasa Libosch.* and prepared *Rehmannia glutinasa Libosch.* These two categories differ in their functions and therapeutic applications: raw *Rehmannia glutinasa Libosch.* has the efficacy of clearing away heat and cooling the blood and nourishing Yin to promote the production of body fluid due to its cold property; prepared *Rehmannia glutinasa Libosch.* is used for nourishing Yin and enriching blood and supplement essence and replenishing marrow. Catalpol is one of the main effective components in *Rehmannia glutinasa Libosch.*, and has pharmaceutical effect such as reducing blood glucose and lipid levels, diuresis, moderating defecating and so on.

Our experiments showed that, when the harvested *Rehmannia glutinasa Libosch.* was dried by various methods such as freeze-drying, shade-drying, sun-drying or oven-drying, or was processed into prepared *Rehmannia glutinasa Libosch.*, the content of catalpol in them decreased more or less. Besides, the content of catalpol in fresh *Rehmannia glutinasa Libosch.* decreased with the drying temperature increasing, and the drying period prolonging, and the color of *Rehmannia glutinasa Libosch.* darkening. However, heating is not the sole factor affecting catalpol content, and even under cryopreservation conditions, the content of catalpol in fresh *Rehmannia glutinasa Libosch.* also decreased.

Therefore, in the present invention, the raw material for extraction is raw *Rehmannia glutinasa Libosch.*, comprising its roots, stalks and leaves.

II. The Screen of Extraction Conditions

1. The Determination of Extraction Solvents

Solution I: Take two parts of 20 g of raw *Rehmannia glutinasa Libosch.*, one part was extracted with water of 10 times the weight of the raw material for 1 h for 3 times, each time make up to the volume of 50 mL. Another part was extracted with 80% aqueous ethanol solution of 10 times the weight of the raw material for 1 h for 3 times, each time make up to the volume of 50 mL. After a ten-fold dilution, these samples were analyzed by HPLC for measuring catalpol content.

Test Results: the extraction rate with water was 1.16%, and after the first extraction, 60% of catalpol was extracted; the extraction rate with 80% ethanol was 2.08%, and after the first extraction, 78% of catalpol was extracted. So, alcohol extraction method was selected for extracting catalpol from raw *Rehmannia glutinasa Libosch.* because of its superior extraction rate.

Solution II: Take two parts of 20 g of raw *Rehmannia glutinasa Libosch.*, one part was extracted with water of 8 times the weight of the raw material for 1 h for 3 times, each time make up to the volume of 50 mL. Another part was extracted with 30% aqueous ethanol solution of 8 times the weight of the raw material for 1 h for 3 times, each time make up to the volume of 50 mL. After a ten-fold dilution, these samples were analyzed by HPLC for measuring catalpol content.

Test Results: the extraction rate of the dry extract with water was 30%, and the purity of catalpol was 95%; the extraction rate of the dry extract with 30% ethanol was 38%, and the purity of catalpol was 96%. It can be seen that extraction with both solvents could obtain catalpol with high purity, but extraction with aqueous ethanol solution leaded to higher extraction rate.

2. Concentration of the Ethanol for Extraction and Extraction Time

| Table of factors level | | | |
|---|---|---|---|
| | Condition | | |
| Level | A Temperature (° C.) | B Time (hr) | C Concentration (%) |
| 1 | 65 | 3 | 30 |
| 2 | 70 | 2 | 50 |
| 3 | 75 | 1 | 70 |

| Orthogonal Test and the Results | | | | | |
|---|---|---|---|---|---|
| No. | A | B | C | D | Extraction Rate (%) |
| 1 | 1 | 1 | 1 | 1 | 0.38 |
| 2 | 1 | 2 | 2 | 2 | 0.33 |
| 3 | 1 | 3 | 3 | 3 | 0.36 |
| 4 | 2 | 1 | 2 | 3 | 0.40 |
| 5 | 2 | 2 | 3 | 1 | 0.32 |
| 6 | 2 | 3 | 1 | 2 | 0.39 |
| 7 | 3 | 1 | 3 | 2 | 0.40 |
| 8 | 3 | 2 | 1 | 3 | 0.36 |
| 9 | 3 | 3 | 1 | 2 | 0.37 |
| K1 | 1.07 | | | | T = 3.31 |
| K2 | 1.18 1.13 | 1.07 | | | |
| K3 | 1.11 | | 1.01 | | |
| R | 1.10 | 1.12 | | | |
| | 1.13 | | 1.12 | | |
| | 1.08 | 1.12 | | | |
| | 0.06 | | 0.17 | | |
| | 0.05 | 0.05 | | | |

Conclusion: As is shown in the above table, the factor B had the greatest effect on the test result, followed by the factor A and then the factor C, and among the factors B, A and C, $B_1$, $A_3$ and $C_1$ were the most preferable ones respectively. So the best extraction process condition for *Rehmannia glutinasa*

*Libosch.* was $A_3B_1C_1$, i.e. the best extraction condition was that the temperature was 75° C., the extraction time was 3 hr and the concentration of ethanol was 30%. However, other solvents or ethanol solutions of other concentrations could also be applicable for the extraction of the effective fraction of *Rehmannia glutinasa Libosch.*, but their performances were inferior.

3. The Selection of Resins
Non-polar Resins: H103, D101, HP10
Polar Resin: NKA-II
Weak-Polar Resin: AB8

To separate the main effective composition, i.e. catalpol from the extract liquid acquired above, different types of resins were investigated: non polar resin H103, D101 and HP10, polar resin NKA-, and weak polar resin AB-8. Firstly, adsorption capacities and elution rate of these resins for catalpol were tested as follows: columns were packed with these resins respectively; a certain amount of extract liquid was loaded on the column to flow through the resin; eluates were collected and analyzed for their catalpol content $L_1$ to value the adsorption capacities of different types of resins for catalpol. The smaller the $L_1$ was, the higher adsorption capacity the resin had for catalpol in the extraction liquid, and vice versa. After adsorption, each resin that had high adsorption capacity was eluted in the same eluting method, and the eluates were collected and analyzed for their catalpol content $L_2$. The higher the $L_2$ was, the better the elution effect was. The detailed results was shown in the table below:

| Results of Resin Performance | | | | | | |
|---|---|---|---|---|---|---|
| Resin Type | H103 | D101 | NKA-II | AB-8 | HP10 | HPD-200 |
| $L_1$ (%) | 2.1 | 3.3 | 93 | 2.0 | 3.5 | 2.8 |
| $L_2$ (%) | 94 | 95.5 | — | 97 | 96.8 | 98.1 |

As shown in the above table, resin NKA-II failed to separate catalpol from the extract liquid of *Rehmannia glutinasa Libosch.*, but resins H103, D101, AB-8, HP10 and HPD-200 were able to separate catalpol with content up to 90% in the final products. Our further investigation showed that other resins, such as HP-20, HP-21, AB-8, D101, D201, HPD-100 and HPD-100A were also suitable for separating catalpol.

4. Concentration of Ethanol for Elution

After the extract liquid was filtrated through macroporous resin H103, besides catalpol, saccharides and other impurities in *Rehmannia glutinasa Libosch.* were also adsorbed on the resin, and moreover there were other free impurities. So, water was firstly used to elute the saccharides and the free impurities until eluate became clear. After analyzed by HPLC, it was found that the water eluate did not contain catalpol, which suggested that catalpol was still left on the resin. Then the adsorbed catalpol was gradiently eluted with aqueous ethanol solutions with different concentrations of 10%, 20%, 30%, 40%, 50% and 60%, and the flow rate was 0.5-5 ml/cm²·min. After analysis, no catalpol was found in the eluate obtained by eluting with aqueous ethanol solutions having a concentration of above 40%, which indicated that catalpol was liable to decompose in ethanol. And the eluate obtained by eluting with aqueous ethanol solution having a concentration of 20% was found to contain the highest yield and purity of catalpol. Therefore, aqueous ethanol solution having the concentration of 20% was used as the eluate, and its amount should be 40 times as much as the raw material. To obtain the final product, the eluate needed to be further concentrated and dried under vacuum, and the optimization method was shown below.

5. The Selection of Drying Method and Temperature

In order to investigate the thermostability of the main effective composition, i.e. catalpol, in the effective fraction of *Rehmannia glutinasa Libosch.*, high temperature test was performed on dried samples of the effective fraction under the conditions listed in the following table, which are used adopted in the high temperature test on medicaments in China.

| High Temperature Test | | | |
|---|---|---|---|
| Storage Temperature | 60□ | | |
| Storage Period | 0 | 5 days | 10 days |
| Catalpol Content | 96% | 94% | 88% |

Then the dried samples of the effective fraction were extracted with 30% aqueous ethanol solution for 5 h, and it was found that catalpol content in the extract did not decrease with the elapse of time but increased gradually. Lastly, in the process of concentration and drying, drying at 95° C. and drying at 60° C. under vacuum had greater effects on the catalpol content: the catalpol content decreased to 8-12% of the original content in the former and to 90-98% of the original content in the latter. In conclusion, catalpol was stable in the process of solvent extraction, but it should be noted that, the temperature must not be too high in concentration and drying process.

Identification and Content Determination of the Effective Fraction of *Rehmannia glutinasa Libosch.* According to the Present Invention 1. Property The effective fraction of *Rehmannia glutinasa Libosch.* according to the present invention is white to pale yellow crystal powder with fragrant odor and slightly sweet taste. It readily dissolves in water and methanol, slightly dissolves in ethanol and acetone, and does not dissolve in ether. Its melting point is 207-209° C., and it decomposes while melting.

2. Identification

1) Chromatograms recorded under the item of the content determination showed that the retention time of the main peak of the sample was accordance with that of the standard sample.

2.) The infrared absorption spectra of the sample were consistent with the standard spectra.

3. Content Determination

The determination was made according to the HPLC method as described in Appendix VI.D in the Pharmacopoeia of People's Republic of China of 2005 version.

Chromatographic conditions and system suitability test: packing material: octadecylsilyl silica gels; mobile phase: acetonitrile-0.1% aqueous phosphoric acid (1:99); detection wavelength: 210 nm. The theoretical plate number calculated with catalpol must not be lower than 3000.

Preparation of Standard solution: accurately weighted standard catalpol was dissolved in methanol to form a solution having a concentration of 0.3 mg/ml.

Preparation of Sample solution to be measured: an accurately weighted sample in the range of about 0.3 g was added to a 100 ml volumetric flask. The sample dissolved with methanol was diluted until reaching the calibration mark, shaken up and filtrated through micropore membrane (0.45 μm) to obtain the sample solution to be measured.

Test method: 10 μl of the standard solution and the sample solution to be measured were taken separately, followed by being injected into liquid chromatography and being measured.

Conclusions: the content of catalpol in the effective fraction of *Rehmannia glutinasa Libosch.* according to the present invention was in the range of 90-99.8% with an average of 96%.

Pharmacology Experiments

In order to prove the advantage and progress of the effective fraction of *Rehmannia glutinasa Libosch.* according to the present invention over the existing similar products, comparisons including pharmacology experiments were made between the effective fraction of *Rehmannia glutinasa Libosch.* according to the present invention and the similar *Rehmannia glutinasa Libosch.* extracts prepared according to the prior art by the present application.

1. Experimental Materials 1.1 Samples

Sample to be tested: the effective fraction of *Rehmannia glutinasa Libosch.* according to the present invention, labeled as A;

Positive Control:

The total glycoside extract from the stalks and leaves of *Rehmannia glutinasa Libosch.* prepared according to the disclosure of CN200410062245, labeled as B,

*Rehmannia glutinasa Libosch.* extract obtained according to the method disclosed in Technologies for Purification and Separation of Iridoid Glycosides from Dried *Rehmannia* Root, *Herald of Medicine*, October 2003, 22(10), labeled as C,

*Rehmannia glutinasa Libosch.* extract obtained according to the method disclosed in Study on Separation and Purification of Catalpol in *Rehmannia glutinasa Libosch.*, *China Journal of Chinese Materia Medica*, June 2004, 29(6), labeled as D,

*Rehmannia glutinasa Libosch.* extract (dark brown powder of iridoid glycosides in raw *Rehmannia glutinasa Libosch.*) obtained according to the method disclosed in Separation and Purification of Carbohydrates and Glycosedes in *Rehmannia glutinasa Libosch.* Using Macroposous Resin, *Journal of Chinese Medicinal Materials*, March 2003, 26(3), labeled as E,

*Rehmannia glutinasa Libosch.* extract obtained according to the method disclosed in Technological Process for Catalpol of *Rehmannia glutinasa Libosch, Lishizhen Medicine and Materia Medica Research,* 2000, 11(4), labeled as F;

dimethyl diguanidine (hereinafter abbreviated as DD): produced by Zhengan (Tianjin) medicine Company Ltd.

alloxan: produced by Sigma, USA kits for detecting glucose: produced by Beijing Xinde Institute of Biological Products 1.2 Main Instruments CHEM 300 semi-automatic biochemical analyzer (Germany)

GT-1640 Jingdu Blood Glucose Meter (Arkray)

1.3 Animals

Male Kunming mice weighing 25-29 g

Raising condition: The mice were housed in a laboratory animal room of 2nd grade that was ventilated regularly with the temperature controlled at 20-24° C. Before the test began, their food taking, activities and feces were observed for one week, and normal mice were selected for further test.

2. Experimental Method and Result 2.1 Preparation of Model Mice Suffered from Alloxan-Induced Hyperglycemia Male mice were selected and firstly fasted for 6 hr, and alloxan was injected into tail vein at a dose of 60 mg/kg. After 72 hr, the mice having blood glucose values >11.1 mol/L were selected as experimental animals and grouped.

2.2 Experimental Method:

The alloxan-induced hyperglycemic mice were randomly divided into groups labeled as normal control, model control, low-dose A, mid-dose A, high-dose A, DD, B, C, D, E and F. Subsequently, intragastric administration was performed for 15 consecutive days. 16 hours after the last administration, the mice were fasted for 8 hr. Blood glucose values before administration, and at 1 hour after administration for 5 days, 10 day and 15 days were tested respectively on blood collected from the inguinal vein, and the results were as follows:

TABLE 1

Effect of the Effective Fraction/Extracts of *Rehmannia glutinasa Libosch.* on Alloxan-Induced Hyperglycemic Mice

| | Dose (mg/Kg) | Mice Number | Blood Glucose Value (mmol/L) | | | |
| --- | --- | --- | --- | --- | --- | --- |
| | | | 0 day | 5 days | 10 days | 15 days |
| Normal Control | | 22 | 5.5 | 6.4 | 6.4 | 5.8 |
| Model Control | | 22 | 19.6$^{\triangle\triangle}$ | 24.3$^{\triangle\triangle}$ | 24.9$^{\triangle\triangle}$ | 21.3$^{\triangle\triangle}$ |
| Low-Dose A | 125 | 22 | 19.5 | 18.9 | 17.5 | 15.3 |
| Mid-Dose A | 250 | 22 | 19.7 | 15.2 | 12.8** | 9.2* |
| High-Dose A | 500 | 22 | 20.0 | 14.2** | 11.9** | 8.7** |
| B | 250 | 22 | 20.1 | 18.7 | 16.4 | 15.9 |
| C | 250 | 22 | 19.8 | 19.1 | 15.7 | 14.8 |
| D | 250 | 22 | 19.6 | 18.2 | 17.2 | 15.6 |
| E | 250 | 22 | 19.8 | 18.6 | 16.1 | 14.9 |
| F | 250 | 22 | 20.5 | 19.9 | 16.3 | 14.6 |
| DD | 500 | 22 | 19.7 | 12.5** | 13.2** | 14.0** |

**P < 0.01,
*P < 0.05 (compared with the model control);
$^{\triangle\triangle}$P < 0.01 (compared with the normal control)

2.3 Preparation of Model Mice with Type II Diabetes

Forty male and female KK diabetes mice weighing about 40 g were separately housed at a temperature of 20-40° C. and fed on a fat-heavy diet and arbitrary amount of water. After being fast food but not fast water for 2 hr, 10 μl blood collected from the tail veins was tested for blood glucose values, and mice having blood glucose value ≥8.0 mmol/L were selected.

2.4 Experimental Method

The mice obtained from the above step were randomly divided into groups labeled as model control, low-dose A, mid-dose A, high-dose A, DD, B, C, D, E and F. Subsequently, intragastric administration was performed once a day for 15 consecutive days. Blood glucose values before administration, and at one hour after administration for 5 days, 10 day and 15 days (fast food but not fast water for two hours after last administration) were tested respectively, and the results were as follows:

TABLE 2

Effect of the Effective Fraction/Extracts of *Rehmannia glutinasa* Libosch.
on the Blood Glucose in the Spontaneous Hyperglycemic KK Mice

| Sample | Dose (mg/kg) | Mice Number | Blood Glucose Valure (mmol/L) | | | |
|---|---|---|---|---|---|---|
| | | | 0 day | 5 days | 10 days | 15 days |
| Model Control | 0.2 ml/kg | 11 | 13.40 ± 2.53 | 14.58 ± 2.95 | 15.92 ± 3.90 | 15.35 ± 4.66 |
| Low-Dose A | 125 | 11 | 12.71 ± 2.25 | 10.97 ± 0.66** | 11.24 ± 1.99* | 9.77 ± 3.12*** |
| Mid-Dose A | 250 | 12 | 13.11 ± 4.81 | 9.96 ± 1.78** | 8.12 ± 3.75** | 6.33 ± 2.39** |
| High-Dose A | 500 | 12 | 13.05 ± 5.01 | 9.60 ± 2.29** | 7.25 ± 1.35*** | 5.12 ± 1.93*** |
| B | 250 | 12 | 13.89 ± 3.11 | 11.01 ± 2.19 | 10.13 ± 1.95 | 9.15 ± 3.18 |
| C | 250 | 12 | 12.89 ± 2.99 | 10.96 ± 4.097 | 10.54 ± 2.10 | 8.97 ± 5.03 |
| D | 250 | 12 | 14.11 ± 3.22 | 12.13 ± 2.73 | 10.35 ± 1.97 | 9.11 ± 3.23 |
| E | 250 | 12 | 13.54 ± 3.65 | 11.75 ± 2.29 | 9.43 ± 2.10 | 9.01 ± 3.72 |
| F | 250 | 12 | 14.13 ± 2.17 | 12.13 ± 4.21 | 10.09 ± 3.41 | 8.99 ± 3.57 |
| DD | 500 | 11 | 13.36 ± 2.85 | 11.16 ± 3.19*** | 10.03 ± 2.11*** | 8.84 ± 4.51*** |

Note:
compared with the model control:
*$p < 0.05$,
**$p < 0.01$,
***$p < 0.001$ 3. Experimental Results 3.1 As shown in Table 1, the model control group significantly differed from the normal control group in respect of the blood glucose values, which indicated the model was successfully established. Compared with the model control group, the positive medicine dimethyl diguanidine group and the mid-dose A group showed dramatic decrease in the fasting blood glucose value after 5 days administration ($P<0.01$), and the high-dose A group and the mid-dose A group also showed dramatic decrease in the fasting blood glucose value after 10 days administration ($P<0.01$). The blood glucose values of the dimethyl diguanidine group first decreased and then increased during the whole administration period, and those in the mid-dose A group and the high-dose A group decreased steadily. So conclusions can be made that, mid-dose A group and high-dose A group had good hypoglycemic effect, wherein a good dose-effect relationship can be observed, and their hypoglycemic effect was more obvious in comparison with the samples B, C, D, E and F from the experimental process and experimental data.

3.2 As shown in Table 2, the KK mice model control group was significantly lower than the groups of dimethyl diguanidine, low-dose A, mid-dose and high-dose in respect of the fasting blood glucose value after 5 days administration ($P<0.01$); the groups of mid-dose and high-dose were significantly lower than the groups of the model control, B, C, D, E and F in respect of the fasting blood glucose value after 10 days administration ($P<0.01$) and after 15 days administration ($P<0.01$). So conclusions can be made that, mid-dose A group and high-dose A group had significant hypoglycemic effect in contrast with the other control medicines.

3.3 It can be found in the above test that the *Rehmannia glutinasa Libosch.* extract according to the present invention was also able to reduce blood lipid, and its lipid-decreasing effect was obvious as compared with other control medicines.

Experimental Study on Catalpol and the *Rehmannia glutinasa Libosch.* Extract for their Effect of Inducing Apoptosis in Acute Nonlymphocytic Leukemia Cell In order to investigate catalpol and the *Rehmannia glutinasa Libosch.* extract according to the present invention for their effect of inducing apoptosis in leukemia cells as well as the mechanism, bone marrows and HL260 cells from 15 patients with acute nonlymphocytic leukemia (ANLL) were mixed with catalpol and co-cultivated for 24 hr, and then different test methods including cytomorphologic means, DNA gel electrophoresis and DNA fragments percentage analysis were adopted to observe the effect on apoptosis in leukemia cells. Then 8 samples of bone marrow cells before and after above treatment were detected for the protein expression of genes bcl22 and c2myc (gene families of B-cell lymphoma/leukemia 22 and cell 2 oncogene) by immunohistochemical method. The result showed that, typical apoptotic morphology and trapezoid-shaped DNA band were observed in each treated sample, but there was no such phenomenon in the control sample; the protein expression of genes bcl22 and c2myc of the bone marrow cells treated with catalpol and the *Rehmannia glutinasa Libosch.* extract was obviously lowered.

Conclusion: catalpol and the *Rehmannia glutinasa Libosch.* extract were able to induce apoptosis in ANLL cell and HL260 cell, and one possible mechanism of the apotosis induction was that catalpol inhibited or lowered the protein expression of genes bcl22 and c2myc.

DNA Fragments Percentage at 24 Hrs after Treatment with Catalpol:

| Group | n | control | HHT($10 - 7$ mol · $L^{-1}$) | Ara2c ($10$ µg · $ml^{-1}$) | PL ($20$ µg · $ml^{-1}$) | HA |
|---|---|---|---|---|---|---|
| ANLL cell | 15 | 24.2 ± 4.3 | 38.1 ± 5.1 | 40.1 ± 8.2 | 39.5 ± 7.9 | 46.2 ± 6.4 |
| HL260 cell | 4 | 10.2 ± 0.2 | 26.1 ± 1.2 | 28.2 ± 1.4 | 30.3 ± 1.2 | 34.3 ± 1.6 |

DNA Fragments Percentage after Treating with the Extract for 24 Hrs

| Group | n | control | HHT($10 - 7$ mol · $L^{-1}$) | Ara2c ($10$ µg · $ml^{-1}$) | PL ($20$ µg · $ml^{-1}$) | HA |
|---|---|---|---|---|---|---|
| ANLL cell | 15 | 22.1 ± 3.8 | 36.2 ± 5.0 | 39.7 ± 7.9 | 37.3 ± 7.9 | 45.2 ± 5.8 |
| HL260 cell | 4 | 10.0 ± 0.1 | 25.3 ± 1.0 | 27.0 ± 1.1 | 30.1 ± 1.2 | 33.1 ± 1.4 |

Note:
$P < 0.05$ for each treatment group in comparison with the control group; $P > 0.05$ among all the sample groups The above result indicated that the *Rehmannia glutinasa Libosch.* extract according to the present invention was effective for acute nonlymphocytic leukemia as well as leukemia of other types, and thus can be used to prepare medicaments for treating leukemia.

Safety Investigation on the Effective Fraction of *Radix Rehmannia*

After toxicological experiment on animals, it was found that the maximum amount of 35.2 g/kg by oral administration did not lead to death of the animal in acute toxicity test, and the LD50 value of intraperitoneal injection administration was 12.15-16.46 g/kg.

BEST MODE FOR CARRYING OUT THE INVENTION

The following examples are preferable embodiments for carrying out the present invention, but they are not intended to limit the scope of the present invention.

Example 1

The Effective Fraction of *Rehmannia glutinasa Libosch*. According to the Present Invention The fresh *Rehmannia glutinasa Libosch*. was sliced into sheets about 1 cm in thickness, and the sheets were extracted at 72° C. with 28% ethanol for 3 hours; then the ethanol was recovered and the extract liquid was concentrated to such an extent that there was no odor of ethanol to obtain the extract; after the extract was dissolved with water of 5 times the weight of the raw material, the resultant solution was filtrated, and then the filtrate was loaded on a column packed with H103 macroporous adsorption resin of twice the weight of the raw material; the column was firstly eluted with water until the water eluate became clear, followed by eluted with 20% ethanol of 40 times the weight of the raw material; finally the ethanol eluate was recovered, concentrated, and dried at 55° C. to obtain the effective fraction of *Rehmannia glutinasa Libosch*. The content of catalpol in this effective fraction was 94.8%.

Example 2

The Effective Fraction of *Rehmannia glutinasa Libosch*. According to the Present Invention The fresh *Rehmannia glutinasa Libosch*. was sliced into sheets about 1 cm in thickness, and the sheets were extracted at 75° C. with 30% ethanol for 3 hours; then the ethanol was recovered and the extract liquid was concentrated to such an extent that there was no odor of ethanol to obtain the extract; after the extract was dissolved with water of 5 times the weight of the raw material, the resultant solution was filtrated, and then the filtrate was loaded on a column packed with H103 macroporous adsorption resin of twice the weight of the raw material; the column was firstly eluted with water until the water eluate became clear, followed by eluted with 20% ethanol of 40 times the weight of the raw material; finally the ethanol eluate was recovered, concentrated, and dried at 60° C. to obtain the effective fraction of *Rehmannia glutinasa Libosch*. The content of catalpol in this effective fraction was 96%.

Example 3

The Effective Fraction of *Rehmannia glutinasa Libosch*. According to the Present Invention The fresh *Rehmannia glutinasa Libosch*. was sliced into sheets about 1 cm in thickness, and the sheets were extracted at 80° C. with 45% ethanol for 2.5 hours; then the ethanol was recovered and the extract liquid was concentrated to such an extent that there was no odor of ethanol to obtain the extract; after the extract was dissolved with water of 7 times the weight of the raw material, the resultant solution was filtrated, and then the filtrate was loaded on a column packed with H103 macroporous adsorption resin of three times the weight of the raw material; the column was firstly eluted with water until the water eluate became clear, followed by eluted with 20% ethanol of 40 times the weight of the raw material; finally the ethanol eluate was recovered, concentrated, and dried at 75° C. to obtain the effective fraction of *Rehmannia glutinasa Libosch*. The content of catalpol in this effective fraction was 93.8%.

Example 4

Capsules of the Effective Fraction of *Rehmannia glutinasa Libosch*. According to the Present Invention Capsules can be prepared by directly filling the effective fraction of *Rehmannia glutinasa Libosch*. according to the present invention into capsule shells, or by mixing it with one or more pharmaceutical excipients for capsules and then filling them into capsule shells.

Example 5

Tables of the Effective Fraction of *Rehmannia glutinasa Libosch*. According to the Present Invention Tables can be prepared by using the effective fraction of *Rehmannia glutinasa Libosch*. according to the present invention together with one or more excipients for tablets by conventional methods for preparing tablets. The usable excipients include but are not limited to starch, dextrin, lactose, sugar powder, calcium sulfate, microcrystalline cellulose, mannitol, magnesium stearate, gelatin, arabic gum, methyl cellulose, sodium carboxymethyl cellulose, low-substituted hydroxypropyl cellulose, hydroxypropyl methylcellulose, povidone, sodium alginate, polyethylene glycol, cross-linked sodium carboxymethyl cellulose, sodium carboxymethyl starch, talc and micro silica.

Example 6

Granules of the Effective Fraction of *Rehmannia glutinasa Libosch*. According to the Present Invention Granules can prepared by using the effective fraction of *Rehmannia glutinasa Libosch*. according to the present invention and one or more excipients for granules by conventional methods for preparing granules. The usable excipients include but are not limited to sucrose, dextrin, citric acid and sodium citrate.

The invention claimed is:

1. An effective fraction of *Rehmannia glutinasa Libosch*. for reducing blood glucose and lipid levels, wherein the effective fraction of *Rehmannia glutinasa Libosch*. contains non-single chemical components produced from *Rehmannia glutinasa Libosch*., wherein the non-single chemical components produced include catalpol in an amount of 50% or more, and wherein the non-single chemical components of the effective fraction are produced by extracting fresh *Reh-* mannia glutinasa Libosch. with water or ethanol, and concentrated to obtain an extract, dissolving the extract with water to obtain a solution, loading the solution on a column packed with macroporous adsorption resin, eluting the loaded solution with ethanol; and recovering the ethanol eluate, wherein the effective fraction of *Rehmannia glutinasa Libosch.* significantly reduces blood glucose levels in comparison to controls.

2. An effective fraction of *Rehmannia glutinasa Libosch.* for reducing blood glucose and lipid levels in accordance with claim 1, characterized in that the content of catalpol in the effective fraction of *Rehmannia glutinasa Libosch.* is in a range of 90%-99.8%.

3. The effective fraction of *Rehmannia glutinasa Libosch.* for reducing blood glucose and lipid levels according to claim 2, characterized in that the content of catalpol in the effective fraction of *Rehmannia glutinasa Libosch.* is 96%.

4. A preparation of *Rehmannia glutinasa Libosch.* for reducing blood glucose and lipid levels in accordance with claim 1, characterized in that the preparation includes pharmaceutical excipients added to the effective fraction of *Rehmannia glutinasa Libosch.*

5. The preparation of *Rehmannia glutinasa Libosch.* according to claim 4, characterized in that the preparation is in the form of tablet, capsule, granule or pill.

6. The effective fraction of *Rehmannia glutinasa Libosch.* for reducing blood glucose and lipid levels according to claim 1, wherein said macroporous adsorption resin is H103, D101, HP10, HP-20, HP-21, AB-8, D101, D201, HPD-100, HPD-200 or HPD-100A; the elution is gradiently eluted with 10-90% ethanol, and wherein the ethanol eluate is concentrated and dried under vacuum at a temperature in the range 50-70° C.

7. The effective fraction of *Rehmannia glutinasa Libosch.* for reducing blood glucose and lipid levels, according to claim 1, wherein the content of catalpol in the effective fraction of *Rehmannia glutinasa Libosch.* is in a range of 90%-99.8%, and fresh *Rehmannia glutinasa Libosch.* is extracted at 60-80° C. with 20-50% ethanol for 2-5 hours; the extract is dissolved with water of 4-6 times the weight of the fresh *Rehmannia glutinasa Libosch.*, the macroporous adsorption resin is 1-3 times the weight of the fresh *Rehmannia glutinasa Libosch.*; 10%-40% ethanol of 30-50 times the weight of fresh *Rehmannia glutinasa Libosch.* is used to elute the solution, and wherein the recovered ethanol eluate is concentrated and dried at 50-70° C.

8. The effective fraction of *Rehmannia glutinasa Libosch.* for reducing blood glucose and lipid levels according to claim 7, wherein the content of catalpol in the effective fraction of *Rehmannia glutinasa Libosch.* is 96%.

9. The effective fraction of *Rehmannia glutinasa Libosch.* for reducing blood glucose and lipid levels according to claim 7, wherein the fresh *Rehmannia glutinasa Libosch.* is extracted at 75° C. with 30% ethanol for 3 hours; the extract is dissolved with water of 5 times the weight of the fresh *Rehmannia glutinasa Libosch.*, the macroporous adsorption resin is twice the weight of the fresh *Rehmannia glutinasa Libosch.*; 20% ethanol of 40 times the weight of fresh *Rehmannia glutinasa Libosch.* is used to elute the solution, and wherein the recovered ethanol eluate is concentrated and dried at 60° C.

10. The effective fraction of *Rehmannia glutinasa Libosch.* of claim 1, wherein the effective fraction is produced from roots, stalks, and leaves of *Rehmannia glutinasa Libosch.*

11. The effective fraction of *Rehmannia glutinasa Libosch.* of claim 10, wherein the effective fraction is a white to pale-yellow powder.

12. The effective fraction of *Rehmannia glutinasa Libosch.* of claim 1, wherein the effective fraction induces apoptosis in leukemia cells.

13. The effective fraction of *Rehmannia glutinasa Libosch.* of claim 1, wherein the effective fraction significantly reduces blood glucose levels at a dose equivalent to at least 250 mg/kg of the effective fraction in mice.

14. The effective fraction of *Rehmannia glutinasa Libosch.* of claim 13, wherein the effective fraction is in a dosage form suitable for administering a dose equivalent to at least 250 mg/kg of the effective fraction in mice.

15. The effective fraction of *Rehmannia glutinasa Libosch,* of claim 13, wherein the effective fraction significantly reduces blood glucose levels at a dose equivalent to at least 500 mg/kg of the effective fraction in mice.

16. The effective fraction of *Rehmannia glutinasa Libosch.* of claim 15, wherein the effective fraction is in a dosage form suitable for administering a dose equivalent to at least 500 mg/kg of the effective fraction in mice.

17. An effective fraction of *Rehmannia glutinasa Libosch.* for reducing blood glucose and lipid levels, wherein the effective fraction of *Rehmannia glutinasa Libosch.* contains non-single chemical components produced from *Rehmannia glutinasa Libosch.*, wherein the non-single chemical components produced include catalpol in an amount of 50% or more, and wherein the non-single chemical components of the effective fraction are produced by extracting the roots, stalks, and leaves of fresh *Rehmannia glutinasa Libosch.* with water or ethanol, and concentrated to obtain an extract, dissolving the extract with water to obtain a solution, loading the solution on a column packed with macroporous adsorption resin, eluting the loaded solution with ethanol; and recovering the ethanol eluate, wherein the effective fraction of *Rehmannia glutinasa Libosch.* is a white to pale-yellow powder having a melting point of about 207-209° C. and wherein the effective fraction of *Rehmannia glutinasa Libosch.* significantly reduces blood glucose levels in comparison to controls.

* * * * *

UNITED STATES PATENT AND TRADEMARK OFFICE
CERTIFICATE OF CORRECTION

| | | |
|---|---|---|
| PATENT NO. | : 9,089,595 B2 | Page 1 of 1 |
| APPLICATION NO. | : 12/669340 | |
| DATED | : July 28, 2015 | |
| INVENTOR(S) | : Ling Zhang | |

It is certified that error appears in the above-identified patent and that said Letters Patent is hereby corrected as shown below:

On the title page item (30), under "Foreign Application Priority Data," please change "2007 1 0130252" to --2007 1 0130252.6--.

Signed and Sealed this
Fifth Day of January, 2016

Michelle K. Lee
*Director of the United States Patent and Trademark Office*